United States Patent [19]

Audiau et al.

[11] Patent Number: 5,236,940

[45] Date of Patent: Aug. 17, 1993

[54] PHARMACEUTICAL COMPOSITIONS, 2-BENZOTHIAZOLAMINE DERIVATIVES, AND THEIR PREPARATION

[75] Inventors: Francois Audiau, Charenton le Pont; Claude James, Paris, both of France

[73] Assignee: Rhone-Poulenc Sante, France

[21] Appl. No.: 758,378

[22] Filed: Sep. 3, 1991

Related U.S. Application Data

[63] Continuation of Ser. No. 499,813, Dec. 13, 1989, abandoned.

[30] Foreign Application Priority Data

Dec. 15, 1988 [FR] France ............................ 88 16548
Jul. 13, 1989 [FR] France ............................ 89 09484

[51] Int. Cl.$^5$ ................. C07D 277/82; A01K 31/425
[52] U.S. Cl. ...................................... 514/367; 548/164
[58] Field of Search ........................ 548/164; 514/367

[56] References Cited

U.S. PATENT DOCUMENTS 4,826,860 5/1989 Johnson .............................. 514/367

FOREIGN PATENT DOCUMENTS 0050551 4/1982 European Pat. Off. .
0282971 9/1988 European Pat. Off. .

OTHER PUBLICATIONS

Chemical Abstracts, vol. 47 No. 10, May 25, 1953, pp. 4771a–4881f.
Chemical Abstracts, vol. 109, No. 5, 1 Aout 1988, p. 57.

*Primary Examiner*—Robert Gerstl
*Attorney, Agent, or Firm*—Morgan & Finnegan

[57] ABSTRACT

Pharmaceutical compositions are disclosed. They are useful for the treatment of medical conditions associated with the effects of glutamate, comprise as active principle, at least one compound of formula:

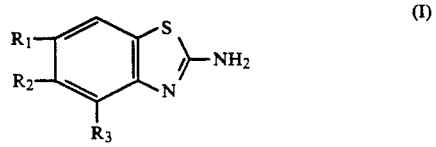

or a salt thereof, in which
  either $R_1$ represents polyfluoroalkoxy, 2,2,2-trifluoroethyl, pentafluoroethyl, tert-butyl, trimethylsilyl or trifluoromethylthio and $R_2$ and $R_3$ represent hydrogen,
  or $R_1$ represents polyfluoroalkoxy, $R_2$ represents hydrogen and $R_3$ represents alkyl, amino, alkoxy, phenyl, phenylalkyl, dimethylamino or dialkylaminoakylthio,
  or $R_1$ represents polyfluoroalkoxy, $R_2$ represents amino and $R_3$ represents hydrogen, with the exception of 6-trifluoromethoxy-2-benzothiazolamine.

11 Claims, No Drawings

PHARMACEUTICAL COMPOSITIONS, 2-BENZOTHIAZOLAMINE DERIVATIVES, AND THEIR PREPARATION

This is a continuation of co-pending U.S. patent application Ser. No. 07/449,813, filed on Dec. 13, 1989 now abandoned.

DESCRIPTION OF THE INVENTION

The present invention provides pharmaceutical compositions comprising, as active principle, usually in association with a compatible pharmaceutical carrier, at least one compound of formula:

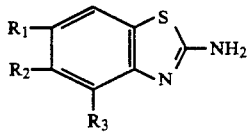

(I)

in which
either $R_1$ represents polyfluoroalkoxy, 2,2,2-trifluoroethyl, pentafluoroethyl, tert-butyl, trimethylsilyl or trifluoromethylthio and $R_2$ and $R_3$ represent hydrogen, or $R_1$ represents polyfluoroalkoxy, $R_2$ represents hydrogen and $R_3$ represents alkyl, amino, alkoxy, phenyl, phenylalkyl, dimethylamino or dialkylaminoakylthio, or $R_1$ represents polyfluoroalkoxy, $R_2$ represents amino and $R_3$ represents hydrogen, provided that, when $R_1$ represents trifluoromethoxy, $R_2$ and $R_3$ are not both hydrogen (i.e. with the exception of 6-trifluoromethoxy-2-benzothiazolamine), and that the said alkyl and alkoxy radicals or portions contain 1 to 4 carbon atoms each in a straight or branched chain, or a salt of such a compound with an inorganic or organic acid.

Preferred polyfluoroalkoxy radicals are pentafluoroethoxy, 2,2,2-trifluoroethoxy, 1,1,2,2-tetrafluoroethoxy, trifluoromethoxy and 2,2,3,3,3,-pentafluoropropoxy.

The compounds of formula (I), with the exception of 6-trifluoromethylthio- and 6-trifluoromethoxy-2-benzothiazolamine, are new and, as such, form part of the invention.

6-Trifluoromethylthio-2-benzothiazolamine is described in Zh. Obshch. Khim., 22, 2216 (1952) (Chem. Abst. 47, 4771 c) and 33(7), 2301 (1963), but no pharmacological property is mentioned for this compound.

The compounds of formula (I) for which
either $R_1$ represents polyfluoroalkoxy, tert-butyl, 2,2,2-trifluoroethyl or pentafluoroethyl and $R_2$ and $R_3$ represent hydrogen, or $R_1$ represents polyfluoroalkoxy, $R_2$ represents hydrogen and $R_3$ represents alkyl, dimethylamino, dialkylaminoalkylthio, alkoxy, phenyl or phenylalkyl may be obtained by the action of bromine and an alkali metal thiocyanate on an amine of formula:

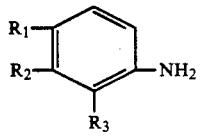

(II)

in which $R_1$, $R_2$ and $R_3$ have the same meanings as above

This reaction is generally performed in an organic solvent such as acetic acid, at a temperature in the region of 20° C. As an alkali metal thiocyanate, potassium thiocyanate is preferably used.

The amines of formula (II) may be prepared by application or adaptation of the methods described in J. Org. Chem., 29, 1 (1964); Beilstein 12, 1166, in patents U.S. Pat. No. 3,920,444, U.S. Pat. No. 2,436,100, DE 3,195,926, DE 2,606,982 and EP 205,821 and in the examples.

The compound of formula (I) for which $R_1$ represents trimethylsilyl and $R_2$ and $R_3$ represent hydrogen may be obtained by the action of chlorotrimethylsilane on the N,N-bis(trimethylsilyl)-2-benzothiazolamine derivative lithiated at the 6-position, obtained by the action of butyllithium and chlorotrimethylsilane on 6-bromo-2-benzothiazolamine, followed by hydrolysis of the N,N-bis(trimethylsilyl) group.

These reactions are performed without separation of the lithium derivative, in an inert solvent such as hexane, tetrahydrofuran or a mixture of these solvents, at a temperature between −70° C. and the boiling point of the medium.

6-Bromo-2-benzothiazolamine may be prepared by application of the method described in Beilstein 27, 184.

The compounds of formula (I) for which $R_1$ represents polyfluoroalkoxy, and either $R_2$ represents amino and $R_3$ represents hydrogen or $R_2$ represents hydrogen and $R_3$ represents amino, may be obtained by reduction of a derivative of formula:

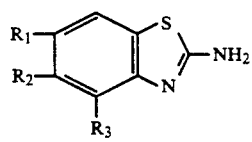

(III)

in which $R_1$ represents polyfluoroalkoxy, and $R_2$ represents nitro and $R_3$ represents hydrogen or $R_2$ represents hydrogen and $R_3$ represents nitro.

This reduction is generally accomplished by means of iron and hydrochloric acid, in an alcohol such as ethanol or methanol, at the boiling point of the solvent.

The compounds of formula (III) may be obtained by nitration of the corresponding 6-polyfluoroalkoxy-2-benzothiazolamine and separation of the two products.

This nitration is generally accomplished by means of a sulphuric/nitric mixture, at a temperature in the region of 0° C.

6-Polyfluoroalkoxy-2-benzothiazolamines may be obtained by application or adaptation of the method described in Zh. Obshch. Khim. 33, 2301 (1963).

The reaction mixtures obtained by the various processes described above are treated according to conventional physical or chemical methods (evaporation, extraction, distillation, crystallization, chromatography, salt formation, etc.).

The compounds of formula (I), in free base form, can be optionally converted into addition salts with an inorganic or organic acid, by the action of such an acid in an organic solvent such as an alcohol, ketone, ether or chlorinated solvent.

The compounds of formula (I) and their salts possess advantageous pharmacological properties. These compounds are useful in the treatment of medical conditions associated with the effects of glutamate in which it is desirable to inhibit such effects at least partially. They are active with respect to glutamate-induced convulsions, and are hence useful in the treatment and prevention of convulsive phenomena, schizophrenic disorders, and in particular the deficiency forms of schizophrenia, sleep disorders, phenomena linked to cerebral ischaemia and also neurological conditions in which glutamate may be implicated, such as Alzheimer's disease, Huntington's chorea, amyotrophic lateral sclerosis and olivopontocerebellar atrophy.

The activity of the compounds of formula (I) with respect to glutamate-induced convulsions was determined according to a technique based on that of I. P. LAPIN, J. Neural. Transmission, vol. 54, 229–238 (1982); intracerebroventricular injection of glutamate being performed according to a technique based on that of R. CHERMAT and P. SIMON, J. Pharmacol. (Paris), vol. 6, 489–492 (1975). Their ED50 does not exceed 10 mg/kg.

The compounds of formula (I) possess low toxicity. Their $LD_{50}$ is generally above 60 mg/kg when administered i.p. in mice.

The following compounds are especially advantageous:
6-pentafluoroethoxy-2-benzothiazolamine,
6-tert-butyl-2-benzothiazolamine,
6-trifluoromethoxy-2,5-benzothiazolediamine,
6-trifluoromethoxy-2,4-benzothiazolediamine.

For medicinal use, the compounds of formula (I) may be employed as they are, or in the form of pharmaceutically acceptable salts, i.e. salts which are non-toxic at the doses at which they are used.

As examples of pharmaceutically acceptable salts, the addition salts with inorganic or organic acids, such as hydrochloride, sulphate, nitrate, phosphate, acetate, propionate, succinate, benzoate, fumarate, maleate, oxalate, methanesulphonate, isethionate, theophyllineacetate, salicylate, phenolphthalinate and methylenebis(β-hydroxynaphthoate), may be mentioned.

EXAMPLES

The examples which follow show how the invention may be put into practice.

EXAMPLE 1

Potassium thiocyanate (8.15 g) is added, while the apparatus is flushed with argon, to a solution of 4-pentaluoroethoxyaniline (4.8 g) in acetic acid (35 cc), and the mixture is stirred for 10 minutes at a temperature in the region of 20° C. To the solution thereby obtained, a solution of bromine (1.1 cc) in acetic acid (10 cc) is introduced dropwise in the course of 35 minutes at a temperature of between 22° and 42° C.; the mixture is thereafter stirred for 20 hours at a temperature in the region of 20° C. The reaction mixture is poured into a mixture of water and ice (250 cc), made alkaline with 28% strength ammonia solution (50 cc) and extracted twice with ethyl acetate (250 cc in total). After settling has taken place, the organic solution is separated and washed with distilled water to pH 8, dried over magnesium sulphate, filtered and evaporated at 50° C. under reduced pressure (20 mm Hg; 2.7 kPa). The product obtained (6.3 g) is purified by chromatography on a column of silica (650 g; particle size: 0.063–0.200 mm) with a mixture of cyclohexane and ethyl acetate (50:50 by volume) as eluant, and recrystallized in boiling cyclohexane (400 cc). 6-Pentafluoroethoxy-2-benzothiazolamine (3.25 g), m.p. 156° C., is obtained.

4-Pentafluoroethoxyaniline may be prepared by the method described by W. A. SHEPPARD, J. Org. Chem., 29, 1 (1964).

EXAMPLE 2

The procedure is as in Example 1, starting with 4-tert-butylaniline (14.9 g), potassium thiocyanate (38.8 g) and bromine (5.1 cc) in acetic acid (150 cc). After purification on a column of silica (700 g; particle size: 0.063–0.200 mm) with a cyclohexane/ethyl acetate mixture (40:60 by volume) as eluant and recrystallization in boiling cyclohexane (450 cc), 6-tert-butyl-2-benzothiazolamine (12.2 g), m.p. 146° C. is obtained.

4-tert-Butylaniline may be prepared according to the method described in BEILSTEIN 12, 1166.

EXAMPLE 3

The procedure is as in Example 1, starting with 4-(2,2,2-trifluoroethoxy)aniline, potassium thiocyanate and bromine in acetic acid, to obtain 6-(2,2,2-trifluoroethoxy)-2-benzothiazolamine, m.p. 134° C.

4-(2,2,2-Trifluoroethoxy)aniline may be prepared according to the method described in U.S. Pat. No. 3,920,444.

EXAMPLE 4

A 1.6 M solution (46 cc) of n-butyllithium in hexane is added, while the apparatus is flushed with nitrogen and with stirring, to a solution, cooled to −70° C., of 6-bromo-2-benzothiazolamine (6.8 g) in anhydrous tetrahydrofuran (100 cc). The temperature is then allowed to rise to about 0° C. and a solution of chlorotrimethylsilane (9.3 cc) in anhydrous tetrahydro-furan (10 cc) is added. After the mixture has returned to a temperature in the region of 20° C., it is brought to reflux for 1 hour 30 minutes. It is then cooled to about −10° C. before adding a portion (19 cc) of the same n-butyllithium solution, and the temperature is allowed to rise to about 0° C. To the light red solution obtained, a solution of chlorotrimethylsilane (4.7 cc) in anhydrous tetrahydrofuran (10 cc) is added and the temperature is allowed to rise to about 20° C. The mixture is then heated to reflux for 4 hours 30 minutes. After returning to a temperature in the region of 20° C., the reaction mixture is poured into water (100 cc) while the temperature is maintained below 25° C. and the mixture is made alkaline with ammonia solution. The lower aqueous phase is extracted 4 times with dichloromethane (200 cc in total) and the organic phases are combined, dried over magnesium sulphate, filtered and evaporated at 40° C. under reduced pressure (20 mm Hg; 2.7 kPa). The orange-colored oil obtained (10.1 g) is chromatographed twice on a column of silica, eluting with a mixture of cyclohexane and ethyl acetate (40:60 by volume). A white solid (0.55 g) is thereby recovered, which solid is with petroleum ether (40°–65° C.) (10 cc) to obtain, after draining and drying under reduced pressure (2 hours at 50° C. at 1 mm Hg; 0.13 kPa), 6-trimethylsilyl-2-benzothiazolamine (0.45 g), m.p. 140° C.

6-Bromo-2-benzothiazolamine may be prepared according to the method described in BEILSTEIN 27, 184.

EXAMPLE 5

The procedure is as in Example 1, starting with 4-trifluoromethylthioaniline (3.85 g), potassium thiocyanate (7 g) and bromine (1 cc) in acetic acid (30 cc). The light brown crude product is taken up with acetic acid (250 cc) at 80° C. and the solution obtained is treated with decolorizing charcoal (0.4 g) and filtered; the filtrate is cooled to about 10° C., diluted with water (150 cc) and alkalinized with 28% strength ammonia solution (400 cc). The precipitate obtained is drained, dried in the air and recrystallized in a mixture of cyclohexane (250 cc) and isopropyl ether (30 cc). 6-Trifluoromethylthio-2-benzothiazolamine (2.9 g), m.p. 155° C., is obtained.

4-Trifluoromethylthioaniline may be prepared according to the method described in U.S. Pat. No. 2,436,100.

EXAMPLE 6

The procedure is as in Example 1, starting with 4-trifluoromethoxy-2-methylaniline (0.65 g), potassium thiocyanate (1.3 g) and bromine (0.35 cc) in acetic acid (12 cc). After purification on a column of silica (200 g; particle size: 0.063–0.200 mm), eluting with a cyclohexane/ethyl acetate mixture (50:50 by volume), the white solid obtained (0.65 g) is ground in cyclohexane (20 cc), drained and dried at 60° C. under reduced pressure (1 mm Hg; 0.13 kPa), to give 4-methyl-6-trifluoromethoxy-2-benzothiazolamine (0.6 g), m.p. 162° C.

4-Trifluoromethoxy-2-methylaniline may be prepared according to the method described in German Patent 3,195,926.

EXAMPLE 7

6-Trifluoromethoxy-5-nitro-2-benzothiazolamine (7.2 g), ethanol (25 cc), water (25 cc), iron powder (8.7 g) and concentrated hydrochloric acid (d=1.19) (1.1 cc) are heated to reflux for 2 hours. After returning to a temperature in the region of 20° C., the mixture is alkalinized with 28% strength ammonia solution (10 cc) and extracted 4 times with ethyl acetate (350 cc in total). The organic solution is evaporated at 50° C. under reduced pressure (20 mm Hg; 2.7 kPa). The product obtained (6.4 g) is purified by chromatography on a column of silica (800 g; particle size: 0.063–0.200 mm), eluting with an ethyl acetate/cyclohexane mixture (90:10 by volume), and recrystallized in toluene (320 cc). 6-Trifluoromethoxy-2,5-benzothiazolediamine (4 g), m.p. 175° C., is obtained.

6-Trifluoromethoxy-5-nitro-2-benzothiazolamine may be prepared in the following manner: a sulphuric/nitric mixture, cooled to about 5° C., prepared from concentrated sulphuric acid (d=1.83) (20 cc) and concentrated nitric acid (d=1.42) (10 cc), is added dropwise and with mechanical stirring to 6-trifluoromethoxy-2-benzothiazolamine (11.7 g) cooled to −1° C. During the addition (25 minutes), the temperature of the reaction mixture is maintained below 5° C., and when the addition is complete, stirring is continued for 30 minutes at between 0° C. and 2° C. The reaction product is then poured into a mixture of water and ice (150 cc) and the resulting mixture is alkalinized with 28% strength ammonia solution (75 cc). The yellow precipitate obtained, which is a mixture of 6-trifluoromethoxy-5-nitro-2-benzothiazolamine and 6-trifluoromethoxy-4-nitro-2-benzothiazolamine, is drained. After chromatography on a column of silica (1 kg; particle size: 0.063–0.200 mm), eluting with a cyclohexane/ethyl acetate mixture (60:40 by volume), 6-trifluoromethoxy-5-nitro-2-benzothiazolamine (9.45 g), m.p. 260° C., and 6-trifluoromethoxy-4-nitro-2-benzothiazolamine (0.9 g), m.p. above 260° C. [Rf=0.28; thin-layer chromatography on silica gel; solvent: cyclohexane/ethyl acetate (50:50 by volume)], are obtained.

6-Trifluoromethoxy-2-benzothiazolamine may be prepared according to the method described by L. M. YAGUPOLSKII et al., Zh. Obshch. Khim. 33, 2301 (1963).

EXAMPLE 8

The procedure is as Example 7, starting with 6-trifluoromethoxy-4-nitro-2-benzothiazolamine, iron powder, concentrated hydrochloric acid and ethanol having a water content of 50% (vol./vol.). After purification on a column of silica with a mixture of cyclohexane and ethyl acetate (10:90 by volume) as eluant, a white solid (1.5 g) is recovered, which solid is recrystallized in toluene (130 cc) to obtain 6-tri-fluoromethoxy-2,4-benzothiazolediamine (1 g), m.p. 206° C.

EXAMPLE 9

The procedure is as in Example 1, starting with 4-(1,1,2,2-tetrafluoroethoxy)aniline (10 g), potassium thiocyanate 18.5 g), bromine (2.4 cc) and acetic acid (80 cc). After purification on a column of silica (1 kg; particle size: 0.063–0.200 mm), eluting with a mixture of cyclohexane and ethyl acetate (50:50 by volume), and recrystallization in toluene (22 cc), 6- 1,1,2,2-tetrafluoroethoxy)-2-benzothiazolamine (2 g), m.p. 161° C., is obtained.

4-(1,1,2,2-Tetrafluoroethoxy)aniline may be prepared according to the method described by W. A. SHEPPARD, J. Org. Chem. 29, 1 (1964).

EXAMPLE 10

Potassium thiocyanate (2.3 g) is added to a solution of 4-(2,2,2-trifluoroethyl)aniline (2.1 g) in acetic acid (25 cc), and the mixture is stirred for 10 minutes at a temperature in the region of 20° C. To the solution thereby obtained, a solution of bromine (0.6 cc) in acetic acid (30 cc) is introduced dropwise in the course of 35 minutes at a temperature of between 20° C. and 35° C. The mixture is then stirred for 16 hours at a temperature in the region of 20° C. The reaction mixture is poured into a mixture of water and ice (150 cc), made alkaline with 28% strength ammonia solution (35 cc) and extracted 3 times with ethyl acetate (170 cc in total). After settling has taken place, the organic solution is separated and washed with distilled water to pH 8, dried over magnesium sulphate, filtered and evaporated at 50° C. under reduced pressure (20 mm Hg; 2.7 kPa). After purification on a first silica column, eluting with a cyclohexane/ethyl acetate mixture (50:50 by volume), a beige solid (1.7 g), m.p. 175° C., is obtained, which solid is chromatographed on silica, in this instance using a mixture of dichloromethane and ethyl acetate (50:50 by volume). 6-(2,2,2-Trifluoro-ethyl)-2-benzothiazolamine (0.8 g), m.p. 186° C., is thereby recovered.

4-(2,2,2-Trifluoroethyl)aniline may be prepared in the following manner: palladinized charcoal (0.17 g) containing 10% of palladium is added to a solution of 4-(2,2,2-trifluoroethyl)nitrobenzene (3.8 g) in ethanol (20 cc), and a solution of hydrazine hydrate (1.8 cc) in ethanol (10 cc) is introduced dropwise and with stirring in the course of 20 minutes; the mixture is then heated to reflux for 15 minutes and the temperature is allowed to return to about 20° C. The catalyst is filtered off, the filtrate is concentrated two-fold under reduced pressure (20 mm Hg; 2.7 kPa), water (30 cc) is added and the mixture is extracted with ethyl acetate (200 cc in total). The organic solution is dried over magnesium sulphate, filtered and evaporated under reduced pressure (20 mm Hg; 2.7 kPa), and the evaporation residue (2.7 g) is purified by chromatography on a column of silica with a mixture of cyclohexane and ethyl acetate (70:30 by volume) as eluant. 4-(2,2,2-Trifluoroethy)aniline (2.3 g) is obtained in the form of a yellow oil, which is used directly in the cyclization stage.

4-(2,2,2-Trifluoroethyl)nitrobenzene may be prepared according to the methods described by S. A. FUQUA et al., J. Org. Chem., 30, 1027 (1965), L. M. YAGUPOLSKII et al., Synthesis, (11), 932 (1980), I. KUMADAKI et al., J. Org. Chem., 53, 3637 (1988).

EXAMPLE 11

The procedure is as in Example 1, starting with 4-pentafluoroethylaniline (14.6 g), potassium thiocyanate (14 g) and bromine (3.6 cc) in acetic acid (150 cc). After purification on a column of silica with a mixture of cyclohexane and ethyl acetate (50:50 by volume) as eluant, a yellow solid (17 g) is obtained, which solid is converted to a hydrochloride by the action of hydrochloric acid dissolved in ethyl ether. The precipitate obtained (16 g) is recrystallized in a mixture of acetone (100 cc) and ethanol (60 cc).

6-Pentafluroethyl-2-benzothiazolamine hydrochloride (3.8 g) m.p. 191° C., is obtained.

4-Pentafluoroethylaniline may be prepared according to the method described in German Patent 2,606,982.

EXAMPLE 12

The procedure is as in Example 1, starting with 2-dimethylamino-4-trifluoromethoxyaniline (2 g), potassium thiocyanate (3.5 g) dissolved in acetic acid (30 cc) and bromine (1.45 g; 0.47 cc). Stirring is maintained for 12 hours at this temperature. The mixture is evaporated to dryness at 80° C. under reduced pressure (20 mm Hg; 2.7 kPa). The residue obtained is taken up with water (100 cc) and the pH is brought to 9-10 with concentrated sodium hydroxide (10N). After extraction with ethyl acetate (2×50 cc), washing of the combined phases with water (2×20 cc), drying over anhydrous magnesium sulphate and evaporating to dryness at 40° C. under reduced pressure (20 mm Hg; 2.7 kPa), a brown oil is isolated, which oil is purified by flash chromatography on a column of silica under a stream of nitrogen at moderate pressure (0.5-1.5 bars), with a dichloromethane/methanol mixture (99:1 by volume). A solid is isolated, which is dissolved in ethyl ether (30 cc), and ethereal hydrogen chloride (6.2N) is added until precipitation is complete. 4-Dimethylamino-6-trifluoromethoxy-2-benzothiazolamine (0.7 g) is thereby isolated in the form of a dihydrochloride, m.p. 184° C.

2-Dimethylamino-4-trifluoromethoxyaniline may be prepared in the following manner: 2-dimethylamino-6-trifluoromethoxyacetanilide (2.9 g) and concentrated sulphuric acid (10N) (40 cc) dissolved in water (40 cc) are heated to 80° C. for 2 hours. After the addition of water (80 cc), neutralization with concentrated sodium hydroxide (10N) to pH 11 and extraction with ethyl acetate (2×100 cc), 2-dimethylamino-4-trifluoromethoxyaniline (2 g), which takes the form of a brown oil, is isolated.

2-Dimethylamino-6-trifluoromethylacetanilide may be prepared in the following manner: sodium cyanoborohydride (6.1 g) is added with stirring at a temperature in the region of 20° C. during 1 hour to 2-amino-6-trifluoromethoxyacetanilide (4.68 g) and paraformaldehyde (6 g) dissolved in acetic acid (120 cc). The mixture is stirred for 12 hours at a temperature in the region of 20° C. After cooling at this temperature and addition of water (120 cc), neutralization with concentrated sodium hydroxide (10N) to pH 9 and extraction with ethyl acetate (2×200 cc), an oil is isolated, which oil is purified by flash chromatography on a silica column under a moderate nitrogen pressure (0.5-1.5 bars), with dichloromethane as eluant. 2-Dimethylamino-6-trifluoromethoxyacetanilide (2.2 g), which takes the form of a yellow oil, is thereby isolated.

2-Amino-6-trifluoromethcxyacetanilide may be prepared in the following manner: 2-nitro-6-trifluoromethoxyacetanilide (13.2 g) and sodium dithionite (34.8 g) dissolved in a mixture of dioxane (200 cc) and water (150 cc) are heated with stirring to a temperature of 65° C. for 1 hour. After cooling to a temperature in the region of 20° C., addition of water (100 cc), extraction with ethyl acetate (250 cc) and drying over anhydrous magnesium sulphate, 2-amino-6-trifluoromethoxyacetanilide (5.7 g), m.p. 80° C. is isolated.

2-Nitro-6-trifluoromethoxyacetanilide may be prepared in the following manner: concentrated sulphuric acid (10N) (755 cc) is added at a temperature of 0° C. and with vigorous stirring to 4-trifluoromethoxyacetanilide (219 g). After 2 hours' stirring at a temperature in the vicinity of 20° C., a mixture of concentrated sulphuric acid (10N) (245 cc) and concentrated nitric acid (11N) (64 cc) is added at a temperature of 10° C. during 1 hour. The reaction mixture is stirred for 12 hours at a temperature in the region of 20° C. Water (2.5 liters) is added to this solution at a temperature of 5° C. The brown solid thereby formed is purified by flash chromatography on a column of silica under a stream of nitrogen at moderate pressure (0.5-1.5 bars), with dichloromethane as eluant. 2-Nitro-4-trifluoromethoxyacetanilide (11.8 g), m.p. 63° C., is thereby isolated.

4-Trifluoromethoxyacetanilide may be prepared according to the method described by W. A. SHEPPARD, J. Org. Chem., 29 (1), 1, 1964.

EXAMPLE 13

The procedure is as in Example 1, starting with 2-(3-dimethylaminoethylthio)-4-trifluoromethoxyaniline (4 g), potassium thiocyanate (5.5 g) dissolved in acetic acid (50 cc) and bromine (2.28g; 0.73 cc). Stirring is maintained for 12 hours at this temperature. The mixture is evaporated to dryness at 80° C. under reduced pressure (20 mm Hg; 2.7 kPa). The residue obtained is taken up with water (10 cc) and the pH is brought to 9-10 with concentrated sodium hydroxide (10N). After extraction with ethyl acetate (2×50 cc), washing of the combined phases with water (2×50 cc), drying with anhydrous magnesium sulphate and evaporation to dryness at 40° C. under reduced pressure (20 mm Hg; 2.7 kPa), the residue is purified by flash chromatography on a column of silica under a stream of nitrogen at moderate pressure (0.5-1.5 bars) and recrystallized in isopropyl ether (40 cc). 4-(3-Dimethylaminoethylthio)-6-trifluoromethoxy-2-benzothiazolamine (3.2 g), m.p. 123° C., is thereby obtained.

2-(3-Dimethylaminoethylthio)-4-trifluoromethoxyaniline may be prepared in the following manner: 6-trifluoromethoxy-2-benzothiazolamine (4.7 g) and potassium hydroxide (14 g) dissolved in water (25 cc) are brought to reflux for 12 hours with stirring. The solution is then cooled to a temperature in the vicinity of 20° C. and (2-chloroethyl)dimethylamine hydrochloride (2.9 g) is added. The solution is brought to a temperature of 50° C. for 3 hours and then cooled to a temperature in the vicinity of 20° C. Water (50 cc) is added and the mixture is extracted with ethyl acetate (2×50 cc). The organic phases are combined, dried over anhydrous magnesium sulphate and concentrated to dryness at 40° C. under reduced pressure (20 mm Hg; 2.7 kPa). The residue obtained is purified by flash chromatography on a silica column under a stream of nitrogen at moderate pressure (0.5–1.5 bars), with a dichloromethane/methanol mixture (95:5 by volume) as eluant. 2-(3-Dimethylaminoethylthio)-4-trifluoro-methoxyaniline (4 g) is obtained.

6-Trifluoromethoxy-2-benzothiazolamine may be prepared according to the method described by L. M. YAGUPOL'SKII et al., Zh. Obshch. Khim. 33, 2301 (1963).

EXAMPLE 14

Potassium thiocyanate (4.27 g) is added to a solution of 4-(2,2,3,3,3-pentafluoropropoxy)aniline (2.65 g) in acetic acid (25 cc), and the mixture is stirred for 10 minutes at a temperature in the region of 20° C. To the solution thereby obtained, a solution of bromine (0.56 cc) in acetic acid (5 cc) is introduced dropwise in the course of 35 minutes at a temperature of between 22° C. and 35° C., and the mixture is then stirred for 16 hours at a temperature in the region of 20° C. The reaction mixture is poured into a mixture of water and ice (150 cc), alkalinized with 28% strength ammonia solution (35 cc) and extracted 3 times with ethyl acetate (170 cc in total). After settling has taken place, the organic solution is separated and washed with distilled water to pH 8, dried over magnesium sulphate, filtered and evaporated at 50° C. under reduced pressure (20 mm Hg; 2.7 kPa). The product obtained (3.2 g) is purified by chromatography on a column of silica (250 g; particle size: 0.063–0.200 mm) with a mixture of cyclohexane and ethyl acetate (50:50 by volume) as eluant, and recrystallized in toluene (15 cc). 6-(2,2,3,3,3-Pentafluoropropoxy)-2-benzothiazolamine (1.27 g), m.p. 147° C., is obtained.

4-(2,2,3,3,3-Pentafluoropropoxy)aniline may be prepared according to the method described in European Patent 205,821.

EXAMPLE 15

The procedure is as in Example 1, starting with 2-methoxy-4-trifluoromethoxyaniline (3.3 g), potassium thiocyanate (6.2 g) dissolved in acetic acid (50 cc) and bromine (2.54 g; 0.8 cc). Stirring is continued for 12 hours at this temperature. The mixture is evaporated to dryness at 80° C. under reduced pressure (20 mm Hg; 2.7 kPa). The residue obtained is taken up with water (10 cc) and the pH is brought to 9–10 with concentrated sodium hydroxide (10N). After extraction with ethyl acetate (2×50 cc), washing of the combined phases with water (2×50 cc), drying over anhydrous magnesium sulphate and evaporation to dryness at 40° C. under reduced pressure (20 mm Hg; 2.7 kPa), 4-methoxy-6-trifluoromethoxy-2-benzothiazolamine (3.6 g), m.p. 195° C., is isolated.

2-Methoxy-4-trifluoromethoxyaniline may be prepared in the following manner: N-(2-methoxy-4-trifluoromethoxyphenyl)-tert-butylcarboxamide (3.9 g) and concentrated hydrochloric acid (12N) (40 cc) dissolved in a mixture of water (120 cc) and dioxane (120 cc) are heated to reflux for 12 hours. After neutralization with concentrated sodium hydroxide (10N) to pH 11 and extraction with ethyl acetate (2×100 cc), 2-methoxy-4-trifluoromethoxyaniline (3.3 g) which takes the form of a brown oil, is isolated.

N-(2-Methoxy-4-trifluoromethoxyphenyl)-tert-butylcarboxamide may be prepared in the following manner: N-(2-hydroxy-4-trifluoromethoxyphenyl)-tert-butylcarboxamide (10.8 g), dissolved in tetrahydrofuran (100 cc), is added at a temperature in the region of 20° C. to sodium hydride (2.25 g), in 50% strength dispersion in liquid paraffin, dissolved in tetrahydro-furan (20 cc). The solution is stirred for 1 hour at a temperature in the vicinity of 20° C. and methyl iodide (6.64 g) is then added. The solution is stirred for 12 hours at a temperature in the vicinity of 20° C. After the addition of water (150 cc), extraction with ethyl acetate (200 cc), drying of the organic phase over anhydrous magnesium sulphate and concentration under reduced pressure (20 mm Hg; 2.7 kPa), an oil is isolated, which oil is purified by flash chromatography on a column of silica under a stream of nitrogen at moderate pressure (0.5–1.5 bars), with a mixture of cyclohexane and ethyl acetate (95:5 by volume) as eluant. N-(2-Methoxy-4-trifluoromethoxyphenyl)-tert-butylcarboxamide (3.9 g), which takes the form of an oil, is isolated.

N-(2-Hydroxy-4-trifluoromethoxyphenyl)-tert-butylcarboxamide may be prepared in the following manner: n-butyllithium (1.6M in hexane) 86 cc) is added during 30 minutes at 0° C. and with stirring to N-(4-trifluoromethoxyphenyl)-tert-butylcarboxamide (26.1 g) dissolved in tetrahydrofuran (200 cc). The mixture is stirred at a temperature of 0° C. for 3 hours. Tributyl borate (86 cc) is then added during 15 minutes and the mixture is left stirring at 0° C. for a further 15 minutes. After the addition of hydrochloric acid (1N) (320 cc) at a temperature in the region of 20° C., the solution is left stirring for 12 hours. After extraction with ethyl ether (100 cc) and concentration to dryness at 20° C. under reduced pressure (20 mm Hg; 2.7 kPa), the residue obtained is dissolved in tetrahydrofuran (200 cc). At a temperature in the region of 20° C., a mixture of hydrogen peroxide (110 volumes, 30%) (110 cc) and saturated sodium carbonate solution (10 cc) is added. This solution is then heated to 50° C. for 1 hour. The cooled reaction mixture is taken up with ethyl acetate (100 cc). This organic phase, washed with sodium thiosulphate (2×100 cc) and then with water (100 cc), is concentrated to dryness at 40° C. under reduced pressure (20 mm Hg; 2.7 kPa). N-(2-Hydroxy-4-trifluoromethoxyphenyl)-tert-butylcarboxamide (7.8 g), m.p. 172° C., is thereby isolated.

N-(4-Trifluoromethoxyphenyl)-tert-butylcarboxamide may be prepared in the following manner: pivaloyl chloride (36.2 g) is added at a temperature in the vicinity of 5° C. and with stirring to 4-trifluoromethoxyaniline (53.1 g) dissolved in toluene 300 cc). The reaction mixture is stirred for 48 hours at a temperature in the region of 20° C. N-(4-Trifluoro-methoxyphenyl)-tert-butylcarboxamide (39 g), m.p. 108° C., is thereby isolated.

EXAMPLE 16

The procedure is as in Example 1, starting with 2-phenyl-4-trifluoromethoxyaniline (1.4 g), potassium thiocyanate (2.1 g) dissolved in acetic acid (15 cc) and bromine (0.88 g; 0.28 cc). Stirring is maintained for 12 hours at this temperature. The mixture is evaporated to dryness at 80° C. under reduced pressure (20 mm Hg; 2.7 kPa). The residue obtained is taken up with water (10 cc) and the pH is brought to 9–10 with concentrated sodium hydroxide (10N). After extraction with ethyl acetate (2×100 cc), washing of the combined organic phases with water (2×50 cc), drying over anhydrous magnesium sulphate and evaporation to dryness at 40° C. under reduced pressure (20 mm Hg; 2.7 kPa), 4-phenyl-6-trifluoromethoxy-2-benzothiazolamine (1.1 g), m.p. 168° C., is isolated.

2-Phenyl-4-trifluoromethoxyaniline may be prepared in the following manner: N-(2-phenyl-4-trifluoromethoxyphenyl)acetamide (1.2 g) and sodium hydroxide (2N) (50 cc) dissolved in dioxane (50 cc) are heated to reflux for 12 hours. After the addition of water (50 cc), extraction with ethyl acetate (2×100 cc) and evaporation to dryness at 40° C. under reduced pressure (20 mm Hg; 2.7 kPa), 2-phenyl-4-tri-fluoromethoxyaniline (1.4 g), which takes the form of an orange-colored oil, is isolated.

N-(2-Phenyl-4-trifluoromethoxyphenyl)acetamide may be prepared in the following manner: dihydroxyphenyl-borane (0.74 g), dissolved in methanol (2.5 cc), is added dropwise under nitrogen and at 25° C. to a mixture of N-(2-bromo-4-trifluoromethoxyphenyl)acetamide (1.5 g) and tetrakis(triphenylphosphine)palladium (0.2 g) in toluene (10 cc). This solution is brought to 80° C. and 2M sodium carbonate solution (5 cc) is added. The mixture is stirred for 6 hours at 80° C. After cooling, extraction with ethyl acetate (2×10 cc), drying of the organic phases over magnesium sulphate and evaporation to dryness at 40° C. under reduced pressure (20 mm Hg; 2.7 kPa), an oil is isolated, which oil is purified by flash chromatography on a column of silica under a stream of nitrogen at moderate pressure (0.5-1.5 bars), with a mixture of cyclohexane and ethyl acetate (75:25 by volume) as eluant. N-(2-Phenyl-4-trifluoromethoxyphenyl)acetamide (1.3 g), m.p. 94° C., is isolated.

N-(2-Bromo-4-trifluoromethoxyphenyl)acetamide may be prepared in the following manner: bromine (8 g; 2.8 cc) is added to a mixture of 4-trifluoromethoxyacetanilide (11 g) dissolved in acetic acid (110 cc) brought to 55° C. The reaction mixture is heated for 6 hours to 55° C., cooled and added to a water/ice mixture (1 liter). N-(2-Bromo-4-trifluoromethoxyphenyl)acetamide (14 g), m.p. 123° C., is thereby isolated directly.

4-Trifluoromethoxyacetanilide may be prepared according to the method described by W. A. SHEPPARD, J. Org. Chem., 29 (1), 1 (1964).

EXAMPLE 17

The procedure is as in Example 1, starting with 2-benzyl-4-trifluoromethoxyaniline (1.5 g), potassium thiocyanate (2.1 g) dissolved in acetic acid (15 cc) and bromine (0.88 g; 0.28 cc). Stirring is maintained for 12 hours at this temperature. The mixture is evaporated to dryness at 80° C. under reduced pressure (20 mm Hg; 2.7 kPa). The residue obtained is taken up with water (10 cc) and the pH is brought to 9-10 with concentrated sodium hydroxide (10N). After extraction with ethyl acetate (2×100 cc), washing of the combined organic phases with water (2×50 cc), drying over anhydrous magnesium sulphate and evaporating to dryness at 40° C. under reduced pressure (20 mm Hg; 2.7 kPa), 4-benzyl-6-trifluoromethoxy-2-benzothiazolamine (1.3 g), m.p. 175° C., is isolated.

2-Benzyl-4-trifluoromethoxyaniline may be prepared in the following manner N-(2-benzyl-4-trifluoromethoxyphenyl)-tert-butylcarboxamide (1.7 g) and concentrated hydrochloric acid (12N) (22 cc) dissolved in water (35 cc) are heated to reflux for 12 hours. After neutralization with concentrated sodium hydroxide (10N) to pH 11, extraction with ethyl acetate (2×50 cc) and evaporation to dryness at 40° C. under reduced pressure (20 mm Hg; 2.7 kPa), 2-benzyl-4-trifluoromethoxyaniline (1.5 g), which takes the form of an orange-colored oil, is isolated.

N-(2-Benzyl-4-trifluoromethoxyphenyl)-tert-butylcarboxamide may be prepared in the following manner: N-(2-hydroxyphenylmethyl-4-trifluoromethoxyphenyl)-tertbutylcarboxamide (11 g), dissolved in carbon disulphide (96 cc), is added dropwise at a temperature of between 30° and 34° C. to a mixture of sodium hydride (1.1 g), in 50% strength dispersion in liquid paraffin, dissolved in carbon disulphide (24 cc). The solution is left for 1 hour at 25° C. and methyl iodide (42.6 g; 19 cc) is added dropwise. The mixture is left stirring at 25° C. overnight. After the addition of saturated ammonium chloride solution (150 cc), extraction with dichloromethane (100 cc), drying over anhydrous magnesium sulphate and concentration under reduced pressure (20 mm Hg; 2.7 kPa), a yellow oil (3.4 g) is isolated. This oil is dissolved directly in toluene (25 cc) with azobisisobutyronitrile (0.07 g) and the mixture is brought to 80° C. Tributyltin hydride (8 cc) is added dropwise and under nitrogen. The solution is left for 45 minutes at 85° C. After evaporation to dryness at 30° C. under reduced pressure (20 mm Hg; 2.7 kPa), the residue obtained is purified by flash chromatography on a column of silica under a stream of nitrogen at moderate pressure (0.5-1.5 bars), with a mixture of cyclohexane and ethyl acetate (95:5 by volume) as eluant. N-(2-Benzyl-4-trifluoromethoxyphenyl)-tert-butylcarboxamide (1.7 g), m.p. 88° C., is isolated.

N-(2-Hydroxyphenylmethyl-4-trifluoromethoxyphenyl)-tert-butylcarboxamide may be prepared in the following manner: n-butyllithium (1.6M in hexane) (75 cc) is added in the course of 30 minutes at 0° C. and with stirring to N-(4-trifluoromethoxy)-tert-butylcarboxamide (15.7 g) dissolved in tetrahydrofuran (75 cc). The mixture is stirred at a temperature of 0° C. for 3 hours. Benzaldehyde (7 g; 6.7 cc) is then added and the mixture is left for 12 hours at 25° C. After the addition of water (200 cc), extraction with ethyl acetate (2·100 cc), drying over magnesium sulphate and concentration under reduced pressure (20 mm Hg; 2.7 kPa), N-(2-hydroxyphenylmethyl-4-trifluoromethoxyphenyl)-tert-butylcarboxamide (14.1 g), m.p. 140° C., is isolated.

The pharmaceutical compositions of the invention comprise at least one compound of formula (I), or a salt of such a compound, in the pure state or in the form of a composition in which it is combined with any other pharmaceutically compatible product, which can be inert or physiologically active, and in particular with a compatible pharmaceutically acceptable carrier. The pharmaceutical compositions may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica. These compositions can also comprise substances other than diluents, e.g. one or more lubricants such as magnesium stearate or talc, a coloring, a coating (dragées) or a varnish.

As liquid compositions for oral administration, solutions, suspensions, emulsions, syrups and elixirs of a pharmaceutically acceptable nature, containing inert diluents such as water, ethanol, glycerol, vegetable oils or liquid paraffin, may be used. These compositions can comprise substances other than diluents, e.g. wetting products, sweeteners, thickeners, flavorings or stabilizers.

The sterile compositions for parenteral administration can preferably be suspensions, emulsions or non-aqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in a sterile injectable medium.

The compositions for rectal administration are suppositories or rectal capsules which contain, apart from the active products, excipients such as cocoa butter, semi-synthetic glycerides or polyethylene glycols.

The compositions for topical administration can be, e.g., creams, ointments, lotions, eye washes, mouth washes, nasal drops or aerosols.

In human therapy, the compounds according to the invention are especially useful in the treatment and prevention of convulsive phenomena, schizophrenic disorders, and in particular the deficiency forms of schizophrenia, sleep disorders, phenomena linked to cerebral ischaemia and also neurological conditions in which glutamate may be implicated, such as Alzheimer's disease, Huntington's chorea, amyotrophic lateral sclerosis and olivopontocerebellar atrophy.

The doses depend on the effect sought, the treatment period and the administration route used; they are generally between 30 and 300 mg per day in oral administration for an adult, with unit doses ranging from 10 to 100 mg of active substance.

Generally speaking, the doctor will determine the appropriate dosage in accordance with the age and weight and all other factors characteristic of the subject to be treated.

The examples which follow illustrate compositions according to the invention.

EXAMPLE A

Hard gelatin capsules containing 50 mg of active product and having the following composition are prepared according to the usual technique:

| | |
|---|---|
| 6-pentafluoroethoxy-2-benzothiazolamine | 50 mg |
| cellulose | 18 mg |
| lactose | 55 mg |
| colloidal silica | 1 mg |
| carboxymethylstarch sodium | 10 mg |
| talc | 10 mg |
| magnesium stearate | 1 mg |

EXAMPLE B

Tablets containing 50 mg of active product and having the following composition are prepared according to the usual technique:

| | |
|---|---|
| 6-tert-butyl-2-benzothiazolamine | 50 mg |
| lactose | 104 mg |
| cellulose | 40 mg |
| polyvidone | 10 mg |
| carboxymethylstarch sodium | 22 mg |
| talc | 10 mg |
| magnesium stearate | 2 mg |
| colloidal silica | 2 mg |
| mixture of hydroxymethylcellulose, glycerol and titanium oxide (72:3.5:24.5) | q.s. 1 finished film-coated tablet weighing 245 mg |

EXAMPLE C

An injectable solution containing 10 mg of active product and having the following composition is prepared:

| | |
|---|---|
| 6-trimethylsilyl-2-benzothiazolamine | 10 mg |
| benzoic acid | 80 mg |
| benzyl alcohol | 0.06 cc |
| sodium benzoate | 80 mg |
| ethanol, 95% | 0.4 cc |
| sodium hydroxide | 24 mg |
| propylene glycol | 1.6 cc |
| water | q.s. 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

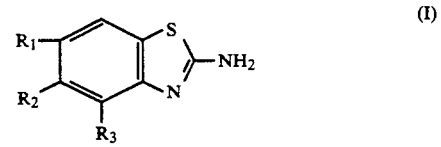

in which either:
(1) - $R_1$ represents polyfluoroalkoxy, tert-butyl, or trimethylsilyl, and $R_2$ and $R_3$ represent hydrogen, with the proviso that, when $R_1$ represents trifluoromethoxy, $R_2$ and $R_3$ are not both hydrogen;
(2) - or $R_1$ represents polyfluoroalkoxy, $R_2$ represents hydrogen, and $R_3$ represents amino or phenylalkyl;
(3) - or $R_1$ represents polyfluoroalkoxy, $R_2$ represents amino and $R_3$ represents hydrogen, provided that said alkyl and alkoxy radicals or portions contain 1to 4 carbon atoms each in a straight or branched chain, or a pharmaceutically acceptable salt of a said compound with an inorganic or organic acid.

2. A compound as claimed in claim 1, in which either:
(1) - $R_1$ represents pentafluoroethoxy, 2,2,2-trifluoroethoxy, 1,1,2,2-tetrafluoroethoxy, or 2,2,3,3,3-pentafluoropropoxy, and $R_2$ and $R_3$ represent hydrogen;

(2) - $R_1$ represents trifluoromethoxy, $R_2$ represents hydrogen, and $R_3$ represents amino;

(3) - $R_1$ represents trifluoromethoxy, $R_2$ represents amino, and $R_3$ represents hydrogen.

3. A compound as claimed in claim 1 which is 6-pentafluoroethoxy-2-benzothiazolamine and its acid addition salts.

4. A compound as claimed in claim 1 which is 6-tert-butyl-2-benzothiazolamine, and its acid addition salts.

5. A compound as claimed in claim 1 which is 6-trifluoromethoxy-2,5-benzothiazolediamine and its acid addition salts.

6. A compound as claimed in claim 1 which is 6-trifluoromethoxy-2,4-benzothiazolediamine and its acid addition salts.

7. A pharmaceutical composition comprising, as active principle, in association with a compatible pharmaceutically acceptable carrier, an effective amount of at least one compound of formula:

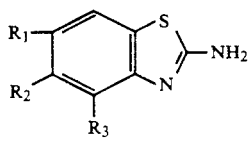

(I)

in which either (1) - $R_1$ represents polyfluoroalkoxy, tert-butyl, or trimethylsilyl and $R_2$ and $R_3$ represent hydrogen, with the proviso that, when $R_1$ represents trifluoromethoxy, $R_2$ and $R_3$ are not both hydrogen;

(2) - or $R_1$ represents polyfluoroalkoxy, $R_2$ represents hydrogen and $R_3$ represents amino or phenylalkyl;

(3) - or $R_1$ represents polyfluoroalkoxy, $R_2$ represents amino and $R_3$ represents hydrogen, provided that said alkyl and alkoxy radicals or portions contain 1 to 4 carbon atoms each in a straight or branched chain, or a pharmaceutically acceptable salt of a said compound with an inorganic or organic acid.

8. A pharmaceutical composition according to claim 7, in which either:

(1) - $R_1$ represents pentafluoroethoxy, 2,2,2-trifluoroethoxy, 1,1,2,2-tetrafluoroethoxy, or 2,2,3,3,3-pentafluoropropoxy, and $R_2$ and $R_3$ represent hydrogen;

(2) - or $R_1$ represents trifluoromethoxy, $R_2$ represents hydrogen, and $R_3$ represents amino;

(3) - or $R_1$ represents trifluoromethoxy, $R_2$ represents amino, and $R_3$ represents hydrogen.

9. A pharmaceutical composition according to claim 7 in which the active ingredient is 6-pentafluoroethoxy-2-benzothiazolamine, 6-tert-butyl-2-benzothiazolamine, 6-trifluoromethoxy-2,5-benzothiazolediamine, or 6-trifluoromethoxy-2,4-benzothiazolediamine.

10. A method for the treatment of a medical condition associated with the effects of glutamate which comprises administering to a subject in need of such treatment an amount of a compound of formula (I) as defined in claim 7 sufficient to inhibit such effects.

11. A method for the treatment of a medical condition associated with the effects of glutamate which comprises administering to a subject in need of such treatment an amount of a compound of formula (I) as defined in claim 8, sufficient to inhibit such effects.

* * * * *